US008231625B2

(12) United States Patent
Graham et al.

(10) Patent No.: US 8,231,625 B2
(45) Date of Patent: Jul. 31, 2012

(54) MODULAR BONE FIXATION DEVICE FOR TREATMENT OF FRACTURES AND RELATED METHODS

(75) Inventors: Thomas James Graham, Timonium, MD (US); Louise M. Focht, Del Mar, CA (US)

(73) Assignee: The Cleveland Clinic Foundation, Cleveland, OH (US)

( * ) Notice: Subject to any disclaimer, the term of this patent is extended or adjusted under 35 U.S.C. 154(b) by 1001 days.

(21) Appl. No.: 12/203,221

(22) Filed: Sep. 3, 2008

(65) Prior Publication Data
US 2010/0057132 A1    Mar. 4, 2010

(51) Int. Cl.
*A61B 17/56* (2006.01)
*A61B 17/58* (2006.01)
*A61B 17/80* (2006.01)
*A61F 2/30* (2006.01)

(52) U.S. Cl. .......... 606/71; 606/280; 606/281; 606/282; 606/286

(58) Field of Classification Search .............. 606/70, 606/71, 282
See application file for complete search history.

(56) References Cited

U.S. PATENT DOCUMENTS

| | | | |
|---|---|---|---|
| 4,164,793 A | 8/1979 | Swanson | 3/1.91 |
| 4,198,712 A | 4/1980 | Swanson | 3/1.91 |
| 4,936,860 A | 6/1990 | Swanson | 623/21 |
| 4,969,908 A | 11/1990 | Swanson | 623/21 |
| 5,314,485 A | 5/1994 | Judet | 623/21 |
| 5,326,364 A | 7/1994 | Clift, Jr. et al. | 623/21 |
| 5,360,431 A | 11/1994 | Puno et al. | 606/72 |
| 5,645,605 A | 7/1997 | Klawitter | 623/21 |
| 5,827,285 A | 10/1998 | Bramlet | 606/60 |
| 5,984,926 A | 11/1999 | Jones | 606/72 |
| 5,984,970 A | 11/1999 | Bramlet | 623/21 |
| 6,221,074 B1 | 4/2001 | Cole et al. | 606/62 |
| 6,283,969 B1 | 9/2001 | Grusin et al. | 606/69 |
| 6,302,887 B1 | 10/2001 | Spranza et al. | 606/73 |
| 6,440,135 B2 | 8/2002 | Orbay et al. | 606/69 |
| 6,475,242 B1 | 11/2002 | Bramlet | 623/21.11 |
| 6,565,960 B2 | 5/2003 | Koob et al. | 428/304.4 |
| 6,699,292 B2 | 3/2004 | Ogilvie et al. | 623/21.15 |
| 6,821,530 B2 | 11/2004 | Koob et al. | 424/458 |

(Continued)

FOREIGN PATENT DOCUMENTS
WO    96/03084    2/1996

(Continued)

OTHER PUBLICATIONS

TONIER US, Medical Professionals, Wrist Products, CoverLoc Volar Plate, 2008.

(Continued)

*Primary Examiner* — Andrew Yang
(74) *Attorney, Agent, or Firm* — Tarolli, Sundheim, Covell & Tummino LLP (57) ABSTRACT

A bone fixation device may include a primary bone plate. The primary bone plate may include an elongate member having a first fastener-receiving passageway therein to receive a first fastener to anchor the primary bone plate to a long bone of a patient, and an enlarged head member extending from the elongate member and having a secondary bone plate-receiving passageway therein. The bone fixation device may also include a secondary bone plate received in the secondary bone plate-receiving passageway and having a second fastener-receiving passageway therein to receive a second fastener to anchor the secondary bone plate to fractured end portions of the long bone of the patient.

22 Claims, 10 Drawing Sheets

U.S. PATENT DOCUMENTS

| | | | |
|---|---|---|---|
| 7,090,676 B2 | 8/2006 | Huebner et al. | 606/71 |
| 7,189,237 B2 | 3/2007 | Huebner | 606/69 |
| 7,326,212 B2 | 2/2008 | Huebner | 606/69 |
| 2004/0097935 A1* | 5/2004 | Richelsoph et al. | 606/61 |
| 2004/0138754 A1 | 7/2004 | Lang et al. | 623/20.14 |
| 2004/0158251 A1 | 8/2004 | Morrison et al. | 606/71 |
| 2005/0049710 A1 | 3/2005 | O'Driscoll et al. | 623/20.11 |
| 2005/0070902 A1 | 3/2005 | Medoff | 606/62 |
| 2005/0216090 A1 | 9/2005 | O'Driscoll et al. | 623/20.32 |
| 2005/0234458 A1 | 10/2005 | Huebner | 606/69 |
| 2005/0245931 A1* | 11/2005 | Orbay | 606/69 |
| 2006/0015101 A1 | 1/2006 | Warburton et al. | 606/62 |
| 2006/0089648 A1 | 4/2006 | Masini | 606/69 |
| 2006/0155284 A1 | 7/2006 | Doherty | 606/69 |
| 2006/0173458 A1 | 8/2006 | Forstein et al. | 606/69 |
| 2007/0014649 A1 | 1/2007 | James | 411/81 |
| 2007/0043357 A1 | 2/2007 | Kirschman | 606/61 |
| 2007/0083202 A1 | 4/2007 | Eli Running et al. | 606/62 |
| 2007/0123867 A1 | 5/2007 | Kirschman | 606/61 |
| 2007/0173834 A1 | 7/2007 | Thakkar | 606/62 |
| 2007/0173841 A1 | 7/2007 | Ralph et al. | 606/69 |
| 2007/0265629 A1 | 11/2007 | Martin et al. | 606/69 |

FOREIGN PATENT DOCUMENTS

| | | |
|---|---|---|
| WO | 01/24717 | 4/2001 |

OTHER PUBLICATIONS

Anatomi$^{design}$, Ascension® PIP PyroCarbon Total Joint.

SBI Small Bone Innovations, SCS™ Volar Distal Radius Plate Sytem, Surgical Technique, 2006, pp. 1-9.

SBI Small Bone Innovations, SCS™Volar Distal Radius Plate, 2008.

* cited by examiner

MODULAR BONE FIXATION DEVICE FOR TREATMENT OF FRACTURES AND RELATED METHODS

FIELD OF THE INVENTION

The present invention relates to the field of surgical implants, and, more particularly, to a bone fixation device for a peri-articular or juxta-articular region of a long bone and related methods.

BACKGROUND OF THE INVENTION

Within the human body, bones are the solid organs that function to move, support, and protect other soft tissue organs in the body. When the human body is subjected to high force impact or stress, the effected bones may fracture. Sometimes, bones may even fracture under less demanding instances due to certain medical conditions (pathologic fractures), for example, Osteoporosis and Osteogenesis Imperfecta, weakening the bone system.

At other times, bones may heal in positions that are mechanically or functionally disadvantageous for normal or optimal functioning (malunions). In these situations, reconstructive surgery, during which bones are cut or "rebroken," may be necessary to restore comfort and improve function.

Fractures of bones may be treated by a variety of methods including, for example, maintaining alignment with casts or splints (closed methods) or operative treatments (open methods). Open treatments for bone fracture may include bone fixation, i.e. open reduction internal fixation (ORIF), where the bone fragments are returned to their normal position for healing and maintained by internal devices and/or external immobilization. When a bone fracture occurs near a joint, i.e. a juxta-articular or peri-articular bone fracture, alignment of the fragments containing articular cartilage surfaces may be important to optimize short-term and long-term outcomes.

After alignment of fragments containing articular cartilage has been achieved, stabilization of the fragments to maintain anatomic alignment during the period of healing is advantageous. A typical bone fixation approach may include surgical implantation of a fastener, for example, a pin, a screw, or a peg, or a bone plate with a fastener construct. The typical bone plate and fastener construct may include an elongate portion with openings for receiving surgical screws or pegs for affixing the bone plate to a diaphysis of the fractured bone, and a flared head portion connected thereto with openings for receiving surgical screws for fixing the fractured portions in an epiphyseal or juxta-articular region of the fractured bone.

An approach to a bone plate is disclosed in U.S. Patent Application Publication No. 2007/0265629 to Martin et al. This bone plate is for treatment of a fracture of the distal portion of a radius bone, which is the bone of the forearm that extends from the lateral side of the elbow to the thumb side of the wrist. The bone plate includes a plurality of fastener openings and a central oblique linking area for aiding in proper placement of the bone plate.

Another approach to a bone plate is disclosed in U.S. Patent Application Publication No. 2006/0173458 to Forstein et al. This bone plate is for treatment of juxta-articular femur bone fractures. This bone plate includes an elongate member with openings for surgical screws, and a flared portion also with openings for surgical screws. This bone plate may be permanently contoured by the surgeon to more accurately fit the femur bone of the patient.

Yet another approach to a bone plate for bone fixation is disclosed in U.S. Pat. No. 7,326,212 to Huebner. This bone plate is also for treatment of distal radius bone fractures and includes an elongate member with openings for surgical screws, and a T-shaped head portion including openings for surgical screws and pivotally coupled to an end of the elongate member. Another distal radius bone plate is disclosed in U.S. Pat. No. 6,283,969 to Grusin et al. This bone plate includes an extender for mating to the flared head portion of the bone plate.

Another approach to a distal radius bone plate is disclosed in U.S. Patent Application Publication No. 2007/0083202 to Eli Running et al. This bone plate includes sheaths for covering the surgical screw heads received by the flared head portion of the bone plate. Each sheath has an opening for receiving a screw for securing the sheath to the bone plate.

Potential drawbacks to the disclosed bone plates are: a lack of cost effectiveness, complexity of implantation, and limitations of the bone plate to engage certain fragments because of the predetermined morphology of the manufactured plate. More particularly, some bone plating systems may use a large inventory of parts for customization to the patient's native anatomy. This may be problematic for cost sensitive environments, for example, in ambulatory surgery centers (ASC) and other outpatient health care facilities in the United States and abroad.

SUMMARY OF THE INVENTION

In view of the foregoing background, it is therefore an object of the present invention to provide a cost effective, modular bone fixation device for treatment of fractures or elective realignments of malunited fractures, particularly those in juxta-articular regions.

This and other objects, features, and advantages in accordance with the present invention are provided by a bone fixation device comprising a primary bone plate. The primary bone plate may include an elongate member having at least one first fastener-receiving passageway therein to receive at least one first fastener to anchor the primary bone plate to a long bone of a patient, and an enlarged head member extending from the elongate member and having at least one secondary bone plate-receiving passageway therein. The bone fixation device may also include at least one secondary bone plate received in the secondary bone plate-receiving passageway and having at least one second fastener-receiving passageway therein to receive at least one second fastener to anchor the secondary bone plate to fractured end portions of the long bone of the patient. Advantageously, the bone fixation device may be used in anatomically diverse patient applications while being cost effective.

In some embodiments, the long bone may comprise a radius bone, and the fractured end portions may comprise fractured distal portions of the radius bone. More specifically, the secondary bone plate-receiving passageway may comprise a plurality thereof, and the secondary bone plate may comprise a plurality thereof with each received in a respective secondary bone plate-receiving passageway. Also, the second fastener-receiving passageway may comprise a plurality thereof, and each secondary bone plate may have a different pattern of the second fastener-receiving passageways therein.

Additionally, the elongate member may define a longitudinal axis, and the secondary bone plate-receiving passageway may comprise a pair thereof arranged in side-by-side relation on opposite sides of the longitudinal axis. In some embodiments, the second fastener-receiving passageway may be angled from normal to the at least one secondary bone plate.

Moreover, the elongate member and the enlarged head member may be connected at a canted angle. The canted angle may be in a range of 5 to 20 degrees. The primary bone plate may have rounded corner portions, and the elongate member may have an arcuate shape. The secondary bone plate-receiving passageway may have a generally rectangular with a corner portion cut therefrom to accommodate variations in patient anatomy.

Another aspect is directed to a method of implanting a bone fixation device for treatment of fractured end portions of a long bone in a patient. The method may comprise providing a primary bone plate. The primary bone plate may include an elongate member having at least one first fastener-receiving passageways therein, and an enlarged head member extending from the elongate member and having at least one secondary bone plate-receiving passageway therein. The method may also include selecting at least one secondary bone plate having at least one second fastener-receiving passageway therein, using at least one first fastener to anchor the primary bone plate to the long bone of the patient, and using at least one second fastener to anchor the secondary bone plate to the fractured end portions of the long bone of the patient.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Referring initially to FIGS. 1-6, a bone fixation device 27 is now described. As will be appreciated by those skilled in the art, the bone fixation device 27 may be used in bone fixation treatments, i.e. open reduction internal fixation (ORIF). The bone fixation device 27 may be used to treat a fractured long bone, for example, the illustrated radius bone 21 (FIG. 1), in a patient, more particularly, a distal juxta-articular radius bone fracture.

As will be appreciated by those skilled in the art, the bone fixation device 27 may be used on other long bones in the patient, for example, the femur bone, the tibia bone, the fibula bones of the legs, and the humerus bones. Moreover, as also appreciated by those skilled in the art, the bone fixation device 27 may be implanted on either the volar side or the dorsal side of the radius bone 21.

Figure 4:
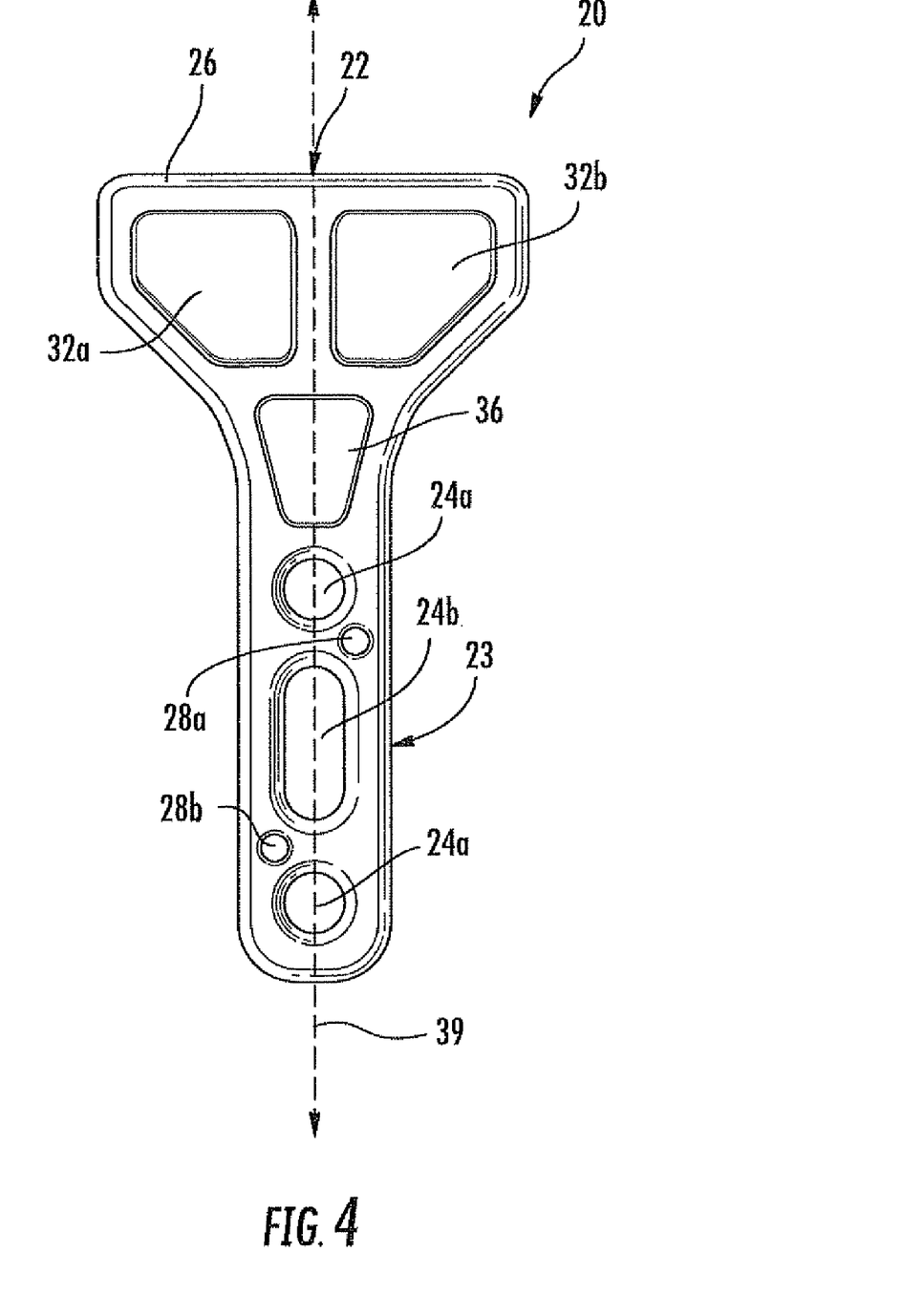
FIG. 4 is a top plan view of the primary bone plate of FIG. 2.
Figure 5:
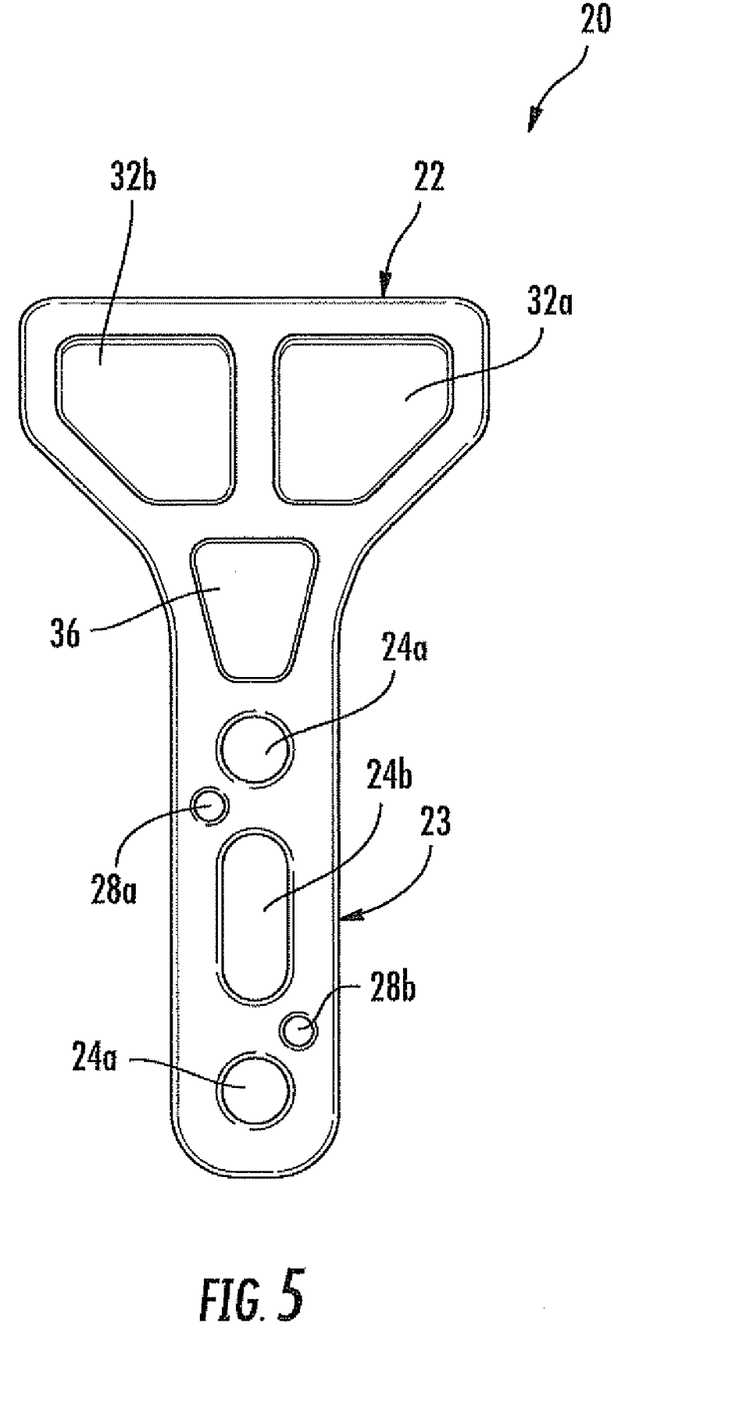
FIG. 5 is a bottom plan view of the primary bone plate of FIG. 2.
Figure 6:
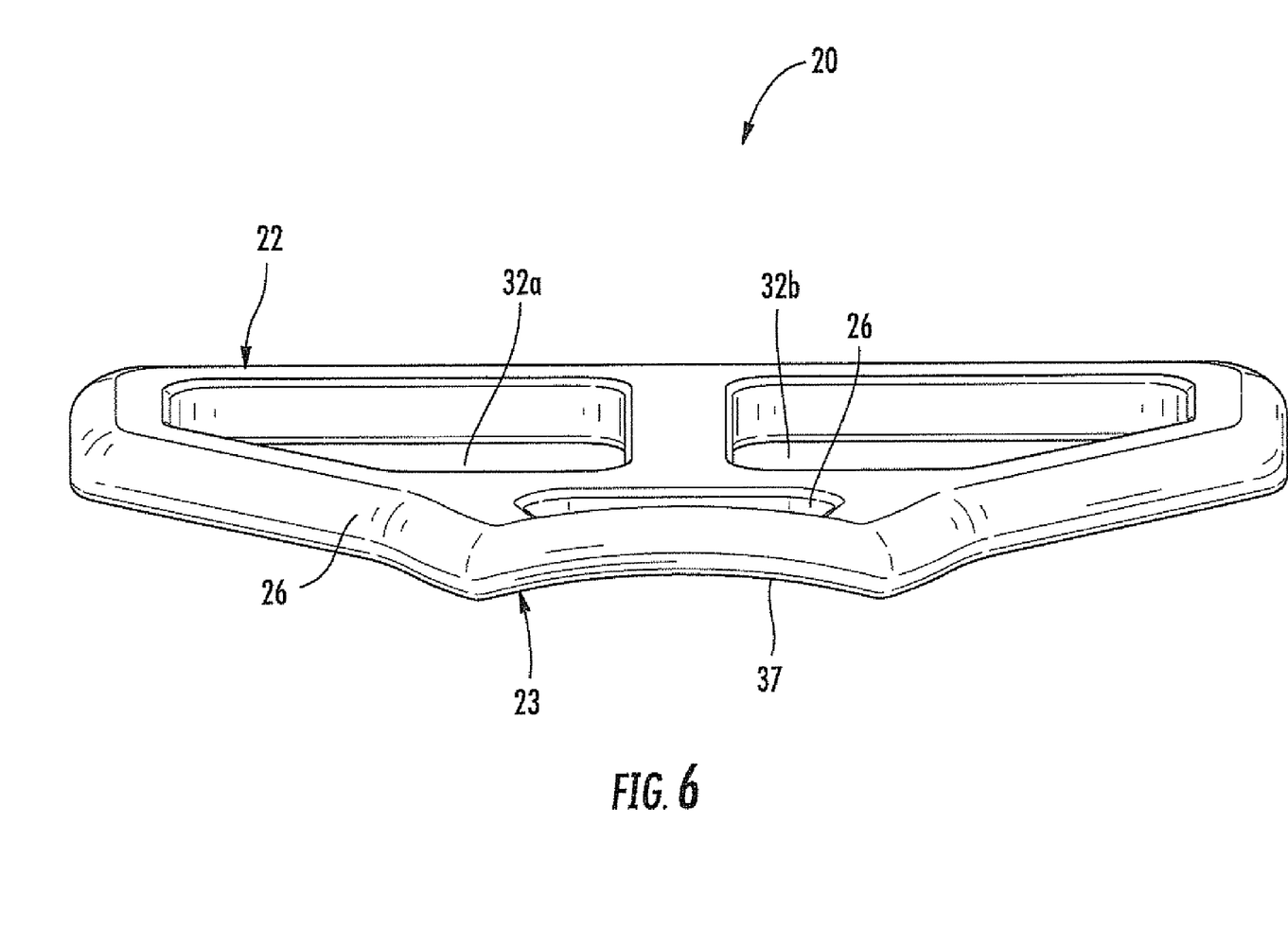
FIG. 6 is a front elevational view of the primary bone plate of FIG. 2.

The bone fixation device 27 illustratively includes a primary bone plate 20 and a plurality of secondary bone plates 30a-30b. The primary bone plate 20 illustratively includes an elongate member 23 having a plurality of first fastener-receiving passageways 24a-24c therein to receive a plurality of first fasteners 25a-25c to anchor the primary bone plate to the radius bone 21 of a patient. More particularly, the elongate member 23 may be anchored to a diaphysis of the radius bone 21. As perhaps best seen in FIG. 6, the elongate member 23 illustratively has an arcuate shape, which may better fit the diaphysis of the radius bone 21. In other words, the primary bone plate 20 is anatomically contoured to match the surface of the radius bone 21. Alternatively, the elongate member 23 can be completely planar or flat. Additionally, the elongate member 23 illustratively defines a longitudinal axis 39 (FIG. 4). The primary bone plate 20 illustratively has rounded corner portions 26, thereby providing greater comfort to the patient after implantation.

The primary bone plate 20 further illustratively includes an enlarged head member 22 extending from the elongate member 23. The angle between the longitudinal axis 39 of the elongate member 23 and the transverse axis of the enlarged head member 22 can be variable and be in the range of approximately 45 to 90 degrees. As perhaps best seen in FIG. 3, the elongate member 23 and the enlarged head member 22 are illustratively connected at a canted angle α of 11 degrees. In other embodiments, the canted angle may be in a range of 5 to 20 degrees.

The enlarged head member 23 illustratively includes a plurality of secondary bone plate-receiving passageways 32a-32b therein. As perhaps best seen in FIG. 1, the secondary bone plates 30a-30b are illustratively received in respective secondary bone plate-receiving passageways 32a-32b. The secondary bone plate-receiving passageways 32a-32b illustratively form a pair thereof arranged in side-by-side relation on opposite sides of the longitudinal axis 39. In the illustrated example, there are two secondary bone plate-receiving passageways 32a-32b (apertures) in the primary bone plate 20 wherethrough it will contact and interface with the secondary bone plates 30a-30b; the number of secondary bone plate-receiving passageways (apertures) for this purpose may vary.

The primary bone plate 20 also illustratively includes a pair of passageways 28a-28b. As will be appreciated by those skilled in the art, these passageways 28a-28b may aid in positioning the primary bone plate 20 and the bone fragments during implantation, for example, by inserting Kirschner wire (K-wire) therethrough. Moreover, the primary bone plate 20 also illustratively includes a medial opening 36. As will be appreciated by those skilled in the art, the medial opening 36 may permit application of bone graft material during implantation to aid in the bone healing process.

Referring now additionally to FIGS. 7-10, each secondary bone plate 30a-30b illustratively includes a plurality of second fastener-receiving passageways 35a-35c, 33a-33c therein to receive a plurality of second fasteners 31a-31f to anchor the secondary bone plates to fractured distal portions of the radius bone 21 of the patient. More particularly, the secondary bone plates 30a-30b fix together the fractured epiphysis of the radius bone 21. As will be appreciated by those skilled in the art, the first 25a-25c and second fasteners 31a-31f may comprise the illustrated surgical screws or pegs, for example.

Figure 9:
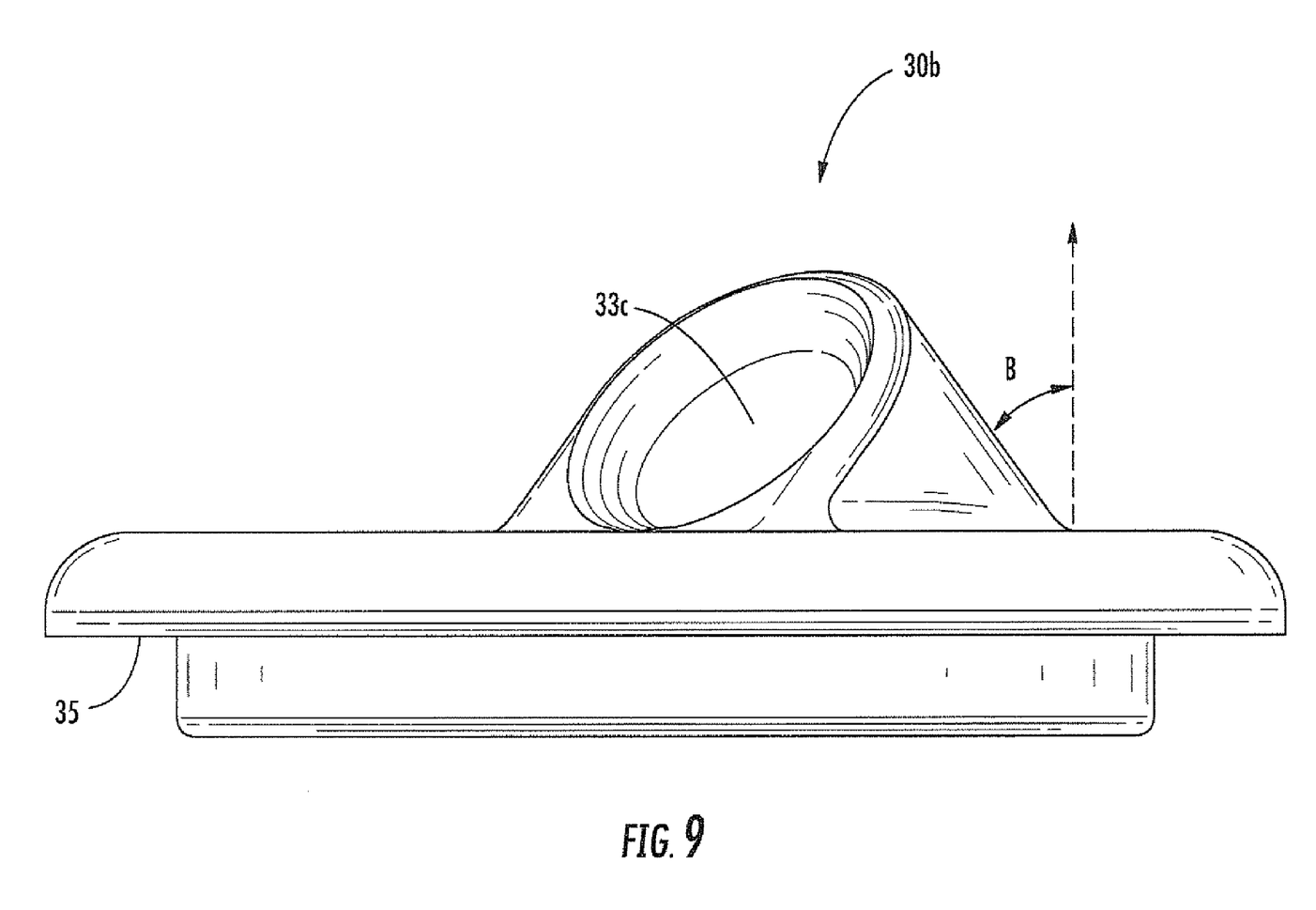
FIG. 9 is a side elevational view of the secondary bone plate of FIG. 7.

As perhaps best seen in FIG. 9, the bottom sides 35 of the secondary bone plates 30a-30b are flanged. Thereby, when the secondary bone plates 30a-30b are inlayed into the secondary bone plate-receiving passageways 32a-32b (apertures) in the enlarged head member 22 of the primary bone plate 20 and the fasteners 31a-31f are inserted into the secondary bone plates 30a-30b, the enlarged head member of the bone fixation device 27 is anchored to the radius bone 21 of the patient by way of cooperation between the flanged bottom sides 35 of the secondary bone plates in their relationship with the internal flange or lip that protrudes into the secondary bone plate-receiving passageways (apertures) in the enlarged head member 22.

In other words, the secondary bone plate-receiving passageways 32a-32b provide a rim or ledge of sorts for the secondary bone plates 30a-30b. Advantageously, each secondary bone plates 30a-30b can be received by both secondary bone plate-receiving passageways 32a-32b, thereby providing flexibility during implantation. Since each secondary bone plate 30a-30b has a different arrangement of the second fastener-receiving passageways 35a-35c, 33a-33c, the secondary bone plates may be oriented to best fit the fracture of the radius bone 21.

In yet other embodiments, not shown, the secondary bone plates 30a-30b may include tabs extending from the sides thereof. The tabs may cooperate with corresponding openings in the secondary bone plate-receiving passageways 32a-32b for aiding in holding the secondary bone plates to the primary bone plate 20 during implantation but before insertion of the second fasteners 31a-31f.

The secondary bone plates 30a-30b and the respective secondary bone plate-receiving passageways 32a-32b illustratively have a generally rectangular shape with a corner portion cut therefrom, but can alternatively be contoured in several ways to still permit the orientation of the secondary bone plates 30a-30b and its passageways (second fastener-receiving passageways 35a-35c, 33a-33c) for fasteners to optimize fracture fragment stabilization. Nonetheless, in other embodiments, not shown, the shape may alternatively be generally rectangular or trapezoidal, for example.

Moreover, as will be appreciated by those skilled in the art, in other embodiments, not shown, the bone fixation device 27 may include more than two secondary bone plates, for example, symmetrically oriented, or only one rotatable secondary bone plate, i.e. the single secondary bone plate may be oriented in a plurality of positions. Indeed, in some embodiments, not shown, the secondary bone plates 30a-30b may have flanged bottom and top sides, thereby permitting the secondary bone plate to be flipped to inverse orientation of the second fastener-receiving passageways 35a-35c, 33a-33c.

Moreover, and as perhaps best seen in FIG. 9, two 33c, 35c of the second fastener-receiving passageways 35a-35c, 33a-33c are illustratively angled from normal to the secondary bone plate 30a-30b, i.e. hooded openings. The angle β (FIG. 9) of canting for the second fastener-receiving passageways 33c, 35c is illustratively 37 degrees. The angle β can be created by either elevating the "hood" that is designed to receive the secondary fastener or recessing the passageway to create a similar angle of passage for the second fasteners 31a-31f into the fracture fragment. As will be appreciated by those skilled in the art, the angled second fastener-receiving passageways 33c, 35c may more readily fix together fragmented portions of the distal radius bone 21. In alternative embodiments, not shown, the secondary bone plates 30a-30b may comprise no angled second fastener-receiving passageways or more than the illustrated two (FIG. 1), i.e. that is one angled second fastener-receiving passageways 33c, 35c for each secondary bone plate 30a-30b. In yet other embodiments, also not shown, some or all of the second fastener-receiving passageways 35a-35c, 33a-33c may be recessed (excavated) and optionally angled, and combined with planar and/or hooded embodiments. In these embodiments, as will be appreciated by those skilled in the art, there may be some relief/gap space underneath the secondary bone plates 30a-30b once coupled to the primary bone plate 20. Advantageously, in these embodiments, the recessed second fastener-receiving passageways may reduce attrition of soft tissue over the implanted bone fixation device 27.

Advantageously, the bone fixation device 27 may be used in cost sensitive applications, i.e. ambulatory surgery centers (ASC), for example, since the facility may stock fewer parts because the surgeon would have the flexibility and capability to build "custom" devices that adapt to a variety of patient anatomies and fracture patterns. To deal with the varied native anatomies and the varied types of distal radius bone 21 fractures treated, the medical facility may stock fewer primary 20 and secondary bone plates 30a-30b. More so, each secondary bone plate 30a-30b illustratively has a different pattern of the second fastener-receiving passageways 35a-35c, 33a-33c therein. Advantageously, by selecting the applicable secondary bone plate 30a-30b, the bone fixation device 27 may be customized to the particular fracture of the radius bone 21 without having to stock of large inventory of differing bone plates. This strategy may optimize patient care while demonstrating a fiscal sensitivity.

Figure 1:
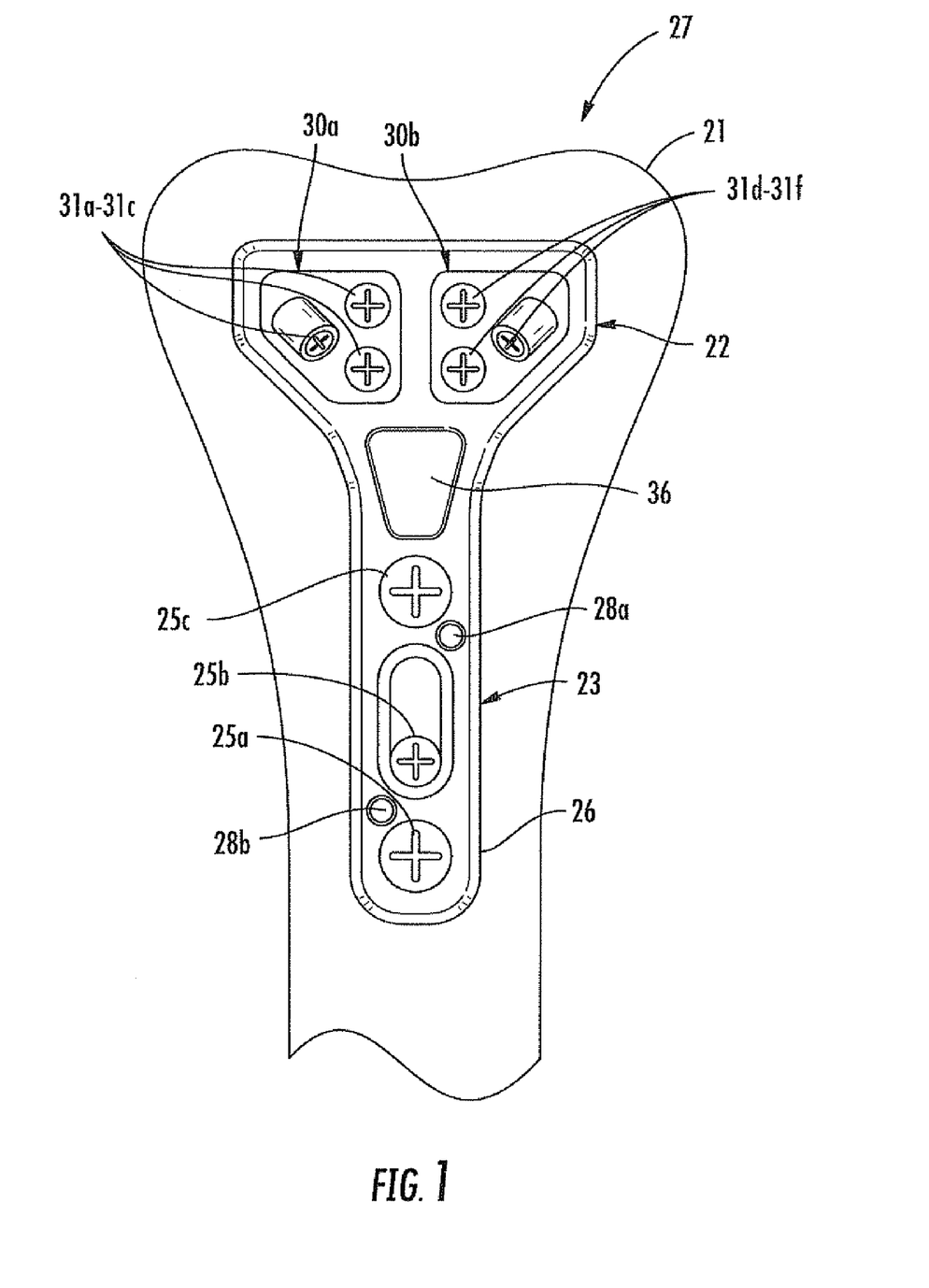
FIG. 1 is a top plan view of the bone fixation device implanted on a radius bone of a patient, according to the present invention.
Figure 2:
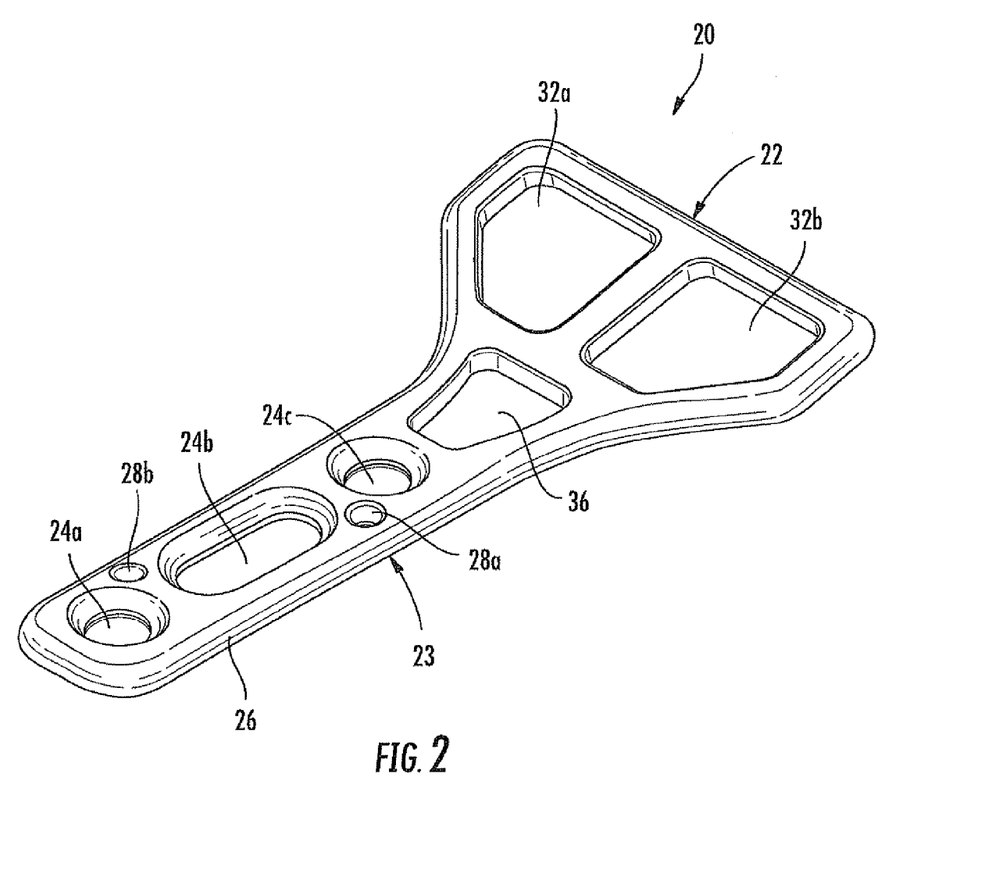
FIG. 2 is a perspective view of the primary bone plate according to the present invention.
Figure 3:
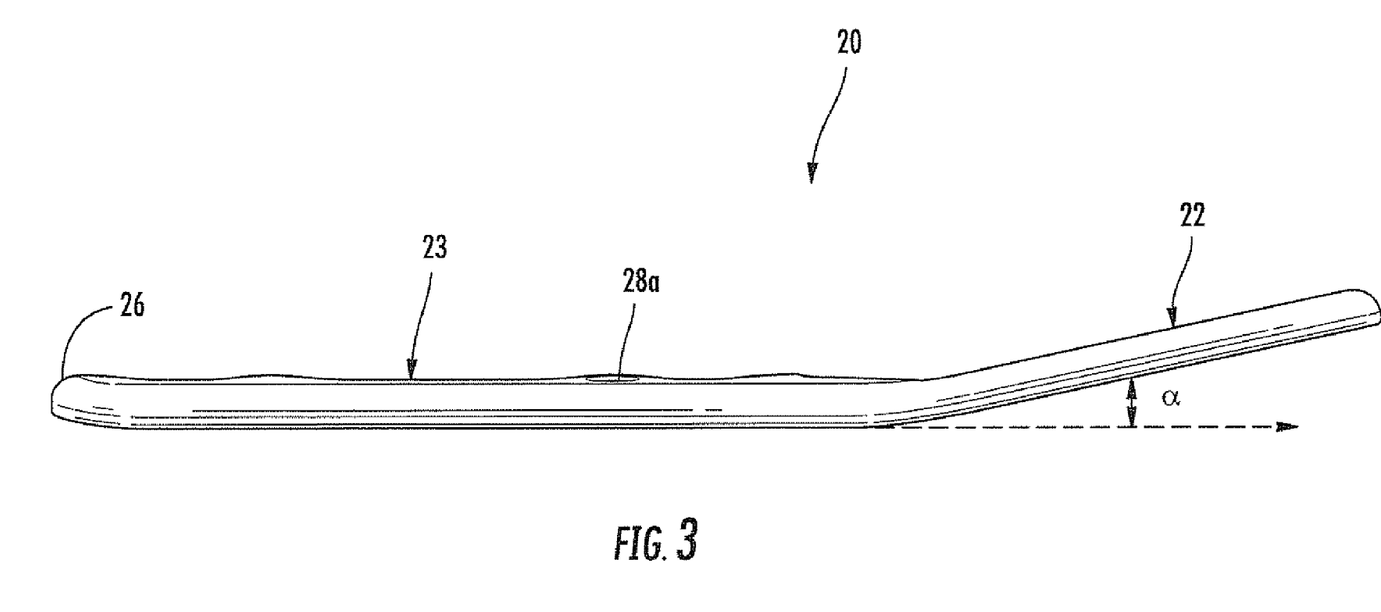
FIG. 3 is a side elevational view of the primary bone plate of FIG. 2.
Figure 7:
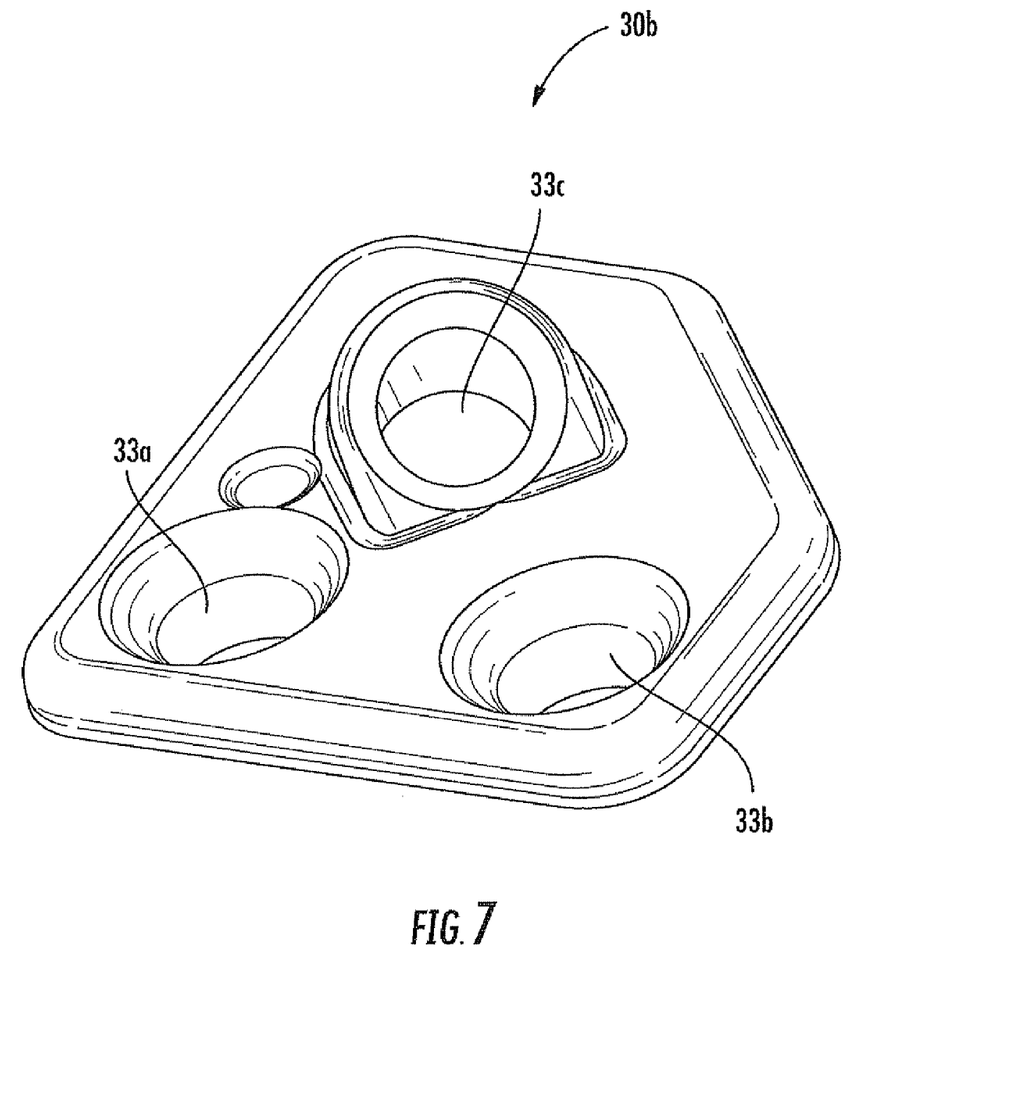
FIG. 7 is a perspective view of the first secondary bone plate according to the present invention.
Figure 8:
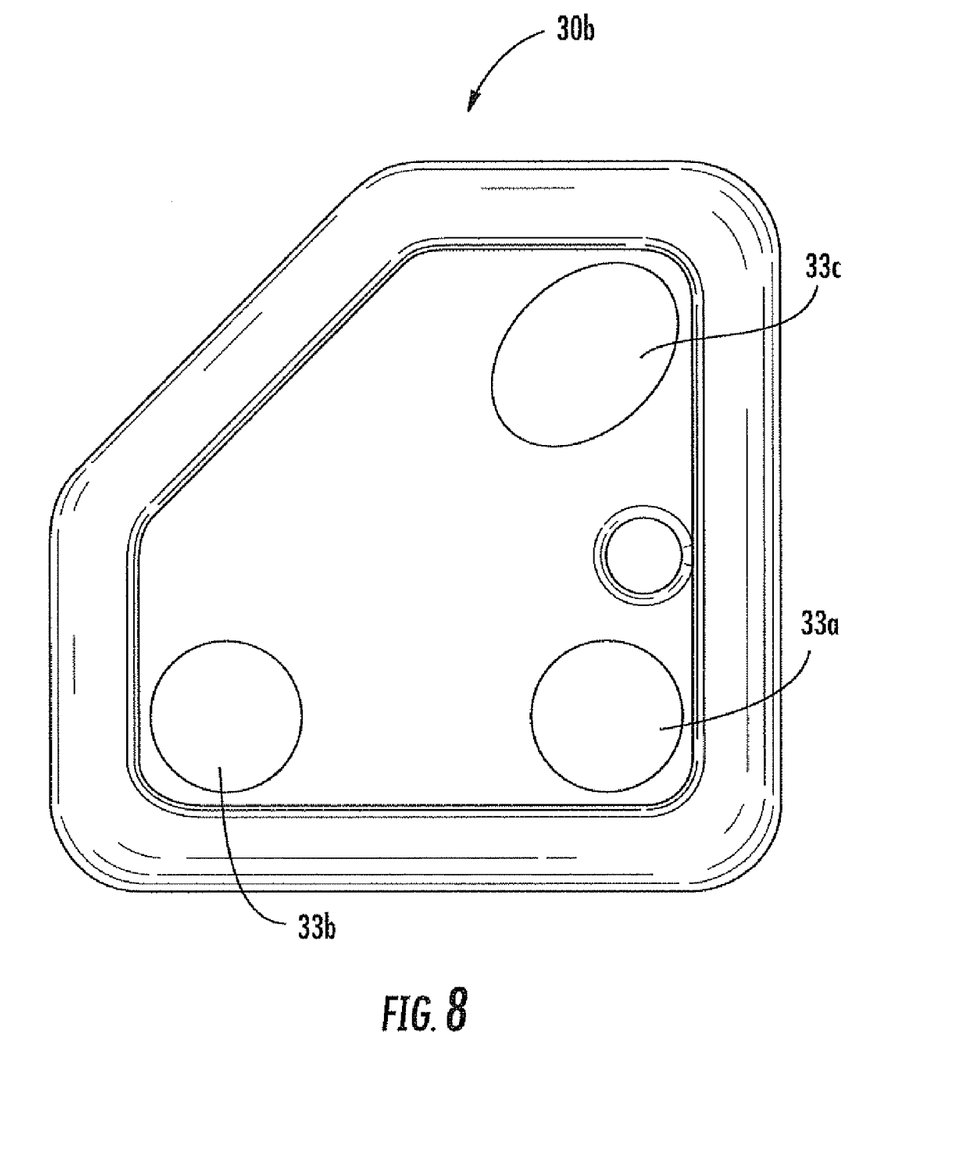
FIG. 8 is a bottom plan view of the secondary bone plate of FIG. 7.
Figure 10:
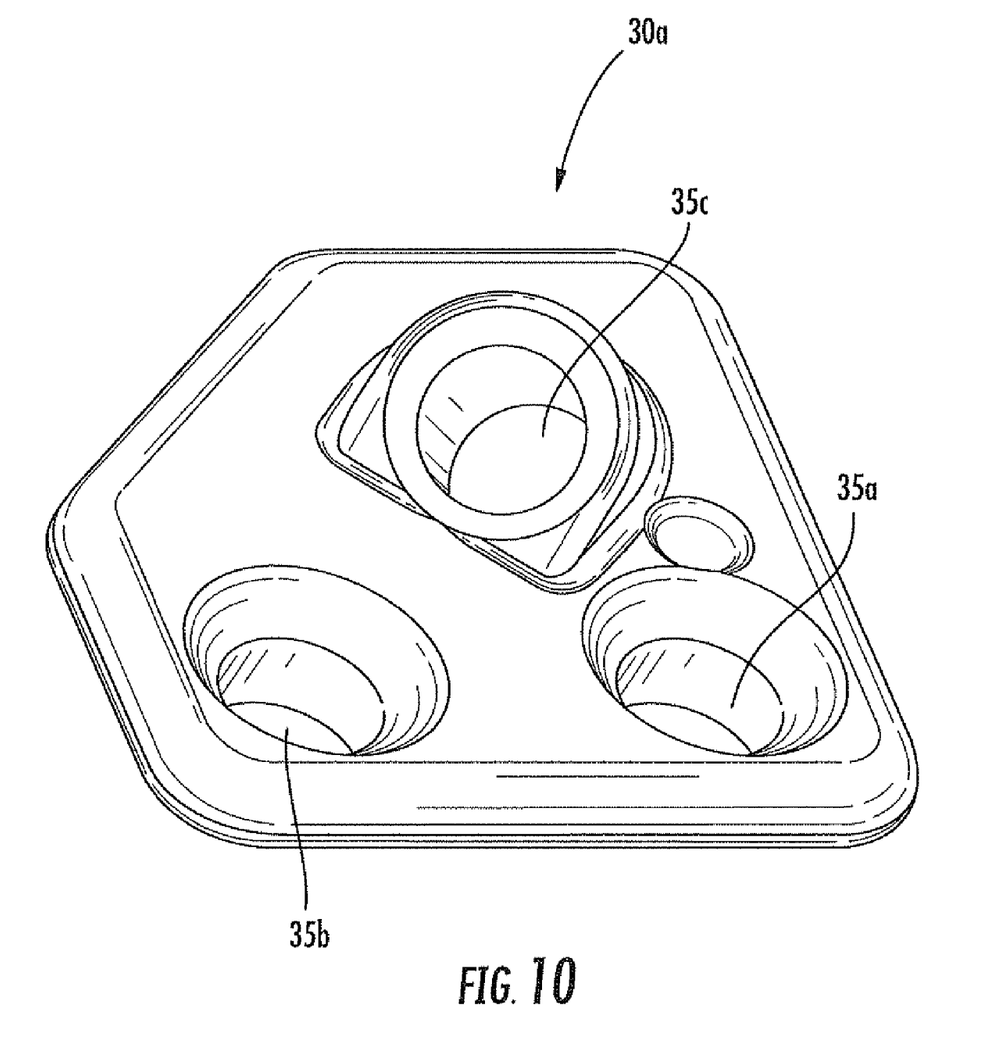
FIG. 10 is a perspective view of another secondary bone plate according to the present invention.

As perhaps best seen in FIGS. 2, 7, and 10, the first fastener-receiving passageways 24a-24c and the second fastener-receiving passageways 35a-35c, 33a-33c are illustratively countersunk. Advantageously, this provides that the head portions of the first 25a-25c and second fasteners 31a-31f do not extend beyond a surface of the elongate member 20 and the secondary bone plates 30a-30b, respectively. Moreover, in some embodiments, not shown, some or all of the first fastener-receiving passageways 24a-24c and the second fastener-receiving passageways 35a-35c, 33a-33c may have threaded surfaces for engaging the threaded surfaces of the respective fasteners considered "locking screws" 25a-25c, 31a-31f, thereby providing a more rigid and durable bone fixation. As will be appreciated by those skilled in the art, elongated passageways, such as the illustrated first fastener-receiving passageway 24b, may or may not have threaded surfaces.

As will be appreciated by those skilled in the art, this bone fixation device 27 may be used in conjunction with supplemental bone fixation devices, for example, as disclosed in U.S. patent application Ser. No. 12/114,619 to Graham et al., also assigned to the present application's assignee.

Another aspect is directed to a method of implanting a bone fixation device 27 for treatment of fractured distal portions of a radius bone 21 in a patient. The method may comprise providing a primary bone plate 22, as described above in detail. The method may also include selecting at least one secondary bone plate 30a-30b, as described above in detail. The method may include using first fasteners 25a-25c to anchor the primary bone plate 22 to the radius bone 21 of the patient, and using second fasteners 31a-31f to anchor the secondary bone plate 20 to the fractured distal portions of the radius bone of the patient. The first fasteners 25a-25c may be implanted before the second fasteners 31a-31f or vice versa.

Other features relating to implants are disclosed in co-pending applications "ARTHROPLASTIC IMPLANT WITH SHIELD FOR BASILAR JOINT AND RELATED METHODS", Ser. No. 12/203,233; "ARTHRODESIS IMPLANT FOR FINGER JOINTS AND RELATED METHODS", Ser. No. 12/203,244; and "ARTHROPLASTIC IMPLANT WITH ANCHOR PEG FOR BASILAR JOINT AND RELATED METHODS", Ser. No. 12/203,259, all incorporated herein by reference in their entirety.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A bone fixation device comprising:
   a primary bone plate comprising:
      an elongate member having at least one first fastener-receiving passageway therein to receive at least one first fastener to anchor said primary bone plate to a long bone of a patient, and
      an enlarged head member extending from said elongate member and having at least one secondary bone plate-receiving passageway therein; and
   at least one secondary bone plate received in the at least one secondary bone plate-receiving passageway and having at least one second fastener-receiving passageway therein to receive at least one second fastener to anchor said at least one secondary bone plate to fractured end portions of the long bone of the patient, the at least one second fastener-receiving passageway being angled from normal to said at least one secondary bone plate, the at least one secondary bone plate-receiving passageway being configured to prevent relative movement between the at least one secondary bone plate-receiving passageway and the at least one secondary bone plate.

2. The bone fixation device according to claim 1 wherein the long bone comprises a radius bone; and wherein the fractured end portions comprise fractured distal portions of the radius bone.

3. The bone fixation device according to claim 1 wherein said elongate member defines a longitudinal axis; and wherein the at least one secondary bone plate-receiving passageway comprises a pair thereof arranged in side-by-side relation on opposite sides of the longitudinal axis.

4. The bone fixation device according to claim 1 wherein said elongate member and said enlarged head member are connected at a canted angle.

5. The bone fixation device according to claim 4 wherein the canted angle is in a range of 5 to 20 degrees.

6. The bone fixation device according to claim 1 wherein said primary bone plate has rounded corner portions.

7. The bone fixation device according to claim 1 wherein said elongate member has an arcuate shape.

8. The bone fixation device according to claim 1 wherein the at least one secondary bone plate-receiving passageway has a generally rectangular shape with a corner portion cut therefrom.

9. The bone fixation device according to claim 1 wherein the at least one secondary bone plate and the at least one bone plate-receiving passageway include cooperating structure that prevents relative movement between the at least one secondary bone plate and the at least one bone plate-receiving passageway.

10. A bone fixation device comprising:
    a primary bone plate comprising
      an elongate member having at least one first fastener-receiving passageway therein to receive at least one first fastener to anchor said primary bone plate to a long bone of a patient, and
      an enlarged head member extending from said elongate member and having a plurality of secondary bone plate-receiving passageways therein; and
    a plurality of secondary bone plates received in the plurality of secondary bone plate-receiving passageways and each having a plurality of second fastener-receiving passageways therein to receive at least one second fastener to anchor said at least one secondary bone plate to fractured end portions of the long bone of the patient, wherein each secondary bone plate has a different pattern of the second fastener-receiving passageways therein, the at least one secondary bone plate-receiving passageway being configured to prevent relative movement between the at least one secondary bone plate-receiving passageway and the at least one secondary bone plate.

11. A bone fixation device comprising:
    a primary bone plate comprising:
      an elongate member having a plurality of first fastener-receiving passageways therein to receive a respective plurality of first fasteners to anchor said primary bone plate to a radius bone of a patient, and
      an enlarged head member extending from said elongate member at a canted angle and having a plurality of secondary bone plate-receiving passageways therein; and
    a plurality of secondary bone plates received in respective secondary bone plate-receiving passageways and each having a plurality of second fastener-receiving passageways therein to receive a respective plurality of second fasteners to anchor said secondary bone plates to fractured distal portions of the radius bone of the patient, wherein each secondary bone plate has a different pattern of second fastener-receiving passageways therein, each secondary bone plate-receiving passageway being configured to prevent relative movement between each secondary bone plate-receiving passageway and each corresponding secondary bone plate.

12. The bone fixation device according to claim 11 wherein said elongate member defines a longitudinal axis; and wherein the secondary bone plate-receiving passageways comprise a pair thereof arranged in side-by-side relation on opposite sides of the longitudinal axis.

13. The bone fixation device according to claim 11 wherein the at least one secondary bone plate and the at least one bone plate-receiving passageway include cooperating structure that prevents relative movement between the at least one secondary bone plate and the at least one bone plate-receiving passageway.

14. A bone fixation device comprising:
    a primary bone plate comprising
      an elongate member having a plurality of first fastener-receiving passageways therein to receive a respective plurality of first fasteners to anchor said primary bone plate to a radius bone of a patient, and an enlarged head member extending from said elongate member at a canted angle and having a plurality of secondary bone plate-receiving passageways therein; and a plurality of secondary bone plates received in respective secondary bone plate-receiving passageways and each having a plurality of second fastener-receiving passageways therein to receive a respective plurality of second fasteners to anchor said secondary bone plates to fractured distal portions of the radius bone of the patient, wherein at least one of the second fastener-receiving passageways is angled from normal to a respective secondary bone plate, each secondary bone plate-receiving passageway being configured to prevent relative movement between each secondary bone plate-receiving passageway and each corresponding secondary bone plate.

15. A method of implanting a bone fixation device for treatment of fractured end portions of a long bone in a patient, the method comprising:

providing a primary bone plate comprising
an elongate member having at least one first fastener-receiving passageway therein, and
an enlarged head member extending from the elongate member and having at least one secondary bone plate-receiving passageway therein;
selecting at least one secondary bone plate having at least one second fastener-receiving passageway therein that is angled from normal to the at least one secondary bone plate, the at least one secondary bone plate-receiving passageway being configured to prevent relative movement between the at least one secondary bone plate-receiving passageway and the at least one corresponding secondary bone plate;
using at least one first fastener to anchor the primary bone plate to the long bone of the patient; and
using at least one second fastener to anchor the at least one secondary bone plate to the fractured end portions of the long bone of the patient.

16. The method according to claim 15 wherein the long bone comprises a radius bone; and wherein the fractured end portions comprise fractured distal portions of the radius bone.

17. The method according to claim 15 wherein the elongate member defines a longitudinal axis; and wherein the at least one secondary bone plate-receiving passageway comprises a pair thereof arranged in side-by-side relation on opposite sides of the longitudinal axis.

18. The method according to claim 15 wherein the elongate member and the enlarged head member are connected at a canted angle.

19. The method according to claim 18 wherein the canted angle is in a range of 5 to 20 degrees.

20. The method according to claim 15 wherein the at least one secondary bone plate-receiving passageway has a generally rectangular shape with a corner portion cut therefrom.

21. The method according to claim 15 further comprising inserting a flange on the at least one secondary bone plate into a cooperating opening in the at least one secondary bone plate-receiving passageway to prevent relative movement between the at least one secondary bone plate and the at least one bone plate-receiving passageway.

22. A method of implanting a bone fixation device for treatment of fractured end portions of a long bone in a patient, the method comprising:

providing a primary bone plate comprising
an elongate member having at least one first fastener-receiving passageway therein, and
an enlarged head member extending from the elongate member and having a plurality of secondary bone plate-receiving passageways therein;
selecting a plurality of secondary bone plates each having a plurality of second fastener-receiving passageways therein, wherein each secondary bone plate has a different pattern of the second fastener-receiving passageways therein, the at least one secondary bone plate-receiving passageway being configured to prevent relative movement between the at least one secondary bone plate-receiving passageway and the at least one corresponding secondary bone plate;
using at least one first fastener to anchor the primary bone plate to the long bone of the patient; and
using at least one second fastener to anchor the at least one secondary bone plate to the fractured end portions of the long bone of the patient.

* * * * *